United States Patent [19] [11] 3,931,829
McWhinnie, Jr. et al. [45] Jan. 13, 1976

[54] VALVED SERVICE OUTLET

[75] Inventors: David A. McWhinnie, Jr.; Laurence G. Viero; Donald J. Freeburg, all of Chicago, Ill.

[73] Assignee: Oxequip Health Industries, Chicago, Ill.

[22] Filed: Nov. 26, 1974

[21] Appl. No.: 527,387

Related U.S. Application Data

[63] Continuation of Ser. No. 375,302, June 29, 1973, abandoned.

[52] U.S. Cl. ......... 137/329.1; 137/361; 137/614.11
[51] Int. Cl.² ......................................... F16L 29/00
[58] Field of Search........... 137/329.1, 329.2, 329.3, 137/329.4, 360, 361, 613, 614.11, 137/614.13, 614.14

[56] References Cited
UNITED STATES PATENTS

| | | | |
|---|---|---|---|
| 2,632,462 | 3/1953 | Selwyn | 137/322 |
| 2,742,052 | 4/1956 | McKee | 137/329.1 |
| 3,441,046 | 4/1969 | Cranage | 137/360 |
| 3,448,760 | 6/1969 | Cranage | 137/360 |
| 3,477,105 | 11/1969 | Cranage | 137/360 |
| 3,563,267 | 2/1971 | Thompson | 137/329.1 |

FOREIGN PATENTS OR APPLICATIONS

| | | | |
|---|---|---|---|
| 1,242,611 | 8/1960 | France | 137/360 |

Primary Examiner—Henry T. Klinksiek
Attorney, Agent, or Firm—Fred Philpitt

[57] ABSTRACT

A valved serviced outlet for oxygen having a number of improved features including an improved guiding and locking means, an improved door, improved valving means and an improved valve body.

5 Claims, 9 Drawing Figures

VALVED SERVICE OUTLET

This is a continuation of application Ser. No. 375,302, filed June 29, 1973, now abandoned.

This is an improvement upon the valved service outlet set forth in U.S. Pat. No. 2,742,052 issued to A. E. McKee on Apr. 17, 1956 and the entire disclosure of that patent is incorporated herein by reference. Since our invention is merely an improvement upon the device shown in U.S. Pat. No. 2,742,052 the purposes, advantages and basic operation of this general type of valve will not be repeated here. The descriptive portion of this application will be confined to an explanation as to how our improved service outlet device differs from the construction set forth in U.S. Pat. No. 2,742,052.

Referring to the attached drawings.

Figure 1:
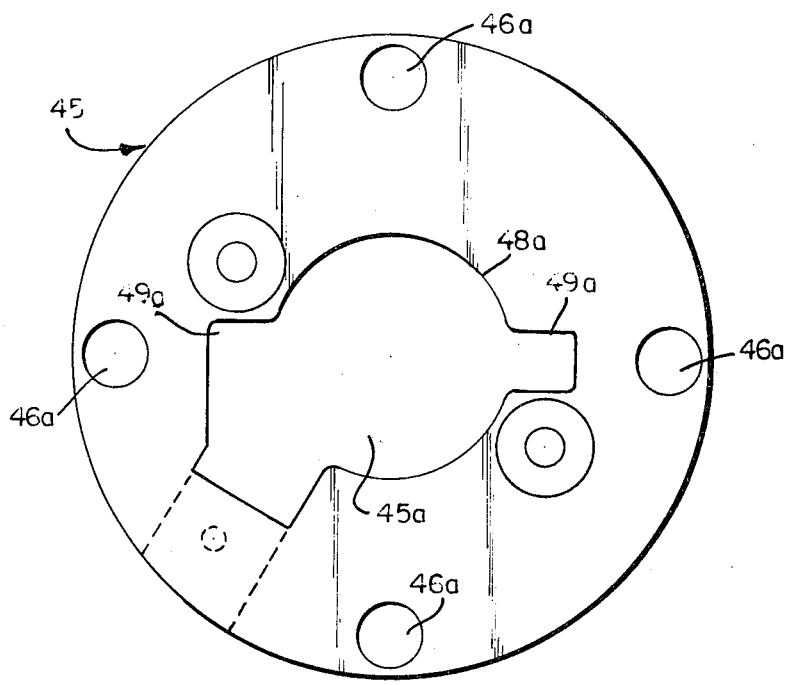
FIG. 1 is an exterior view of our novel camplate.

In FIGS. 3, 4, 6 and 7 of U.S. Pat. No. 2,742,052 it will be seen that cam surfaces 50, which gradually rise until they meet grooves 51, are provided on the backside of the cover plate 45 so that when the tube 60 having pins 61 is inserted through the keyhole opening 48, and the tube 60 is rotated, the pins 61 will ride up the cam surfaces 50 and then drop into the grooves 51. A problem with this construction is that the inclined cam surface (which was molded die cast of relatively soft metal) will eventually wear down to such an extent that the cam surface becomes level (i.e. has no rise), which means that it will then not be possible for the pins 61 to drop into a groove so as to hold the pins against rotation. When this happens, the situation can only be remedied by taking off the entire cover plate (or camplate) and replacing it with a new cover plate (or camplate) that has a cam surface that is properly inclined upwardly toward a locking groove. However, as a practical matter in busy hospitals, nurses will sometimes be inclined to "make do" with an improperly operating camplate either because they do not know that the improperly operating outlet could be remedied or because the hospital maintenance men are too busy with other matters.

Figure 2:
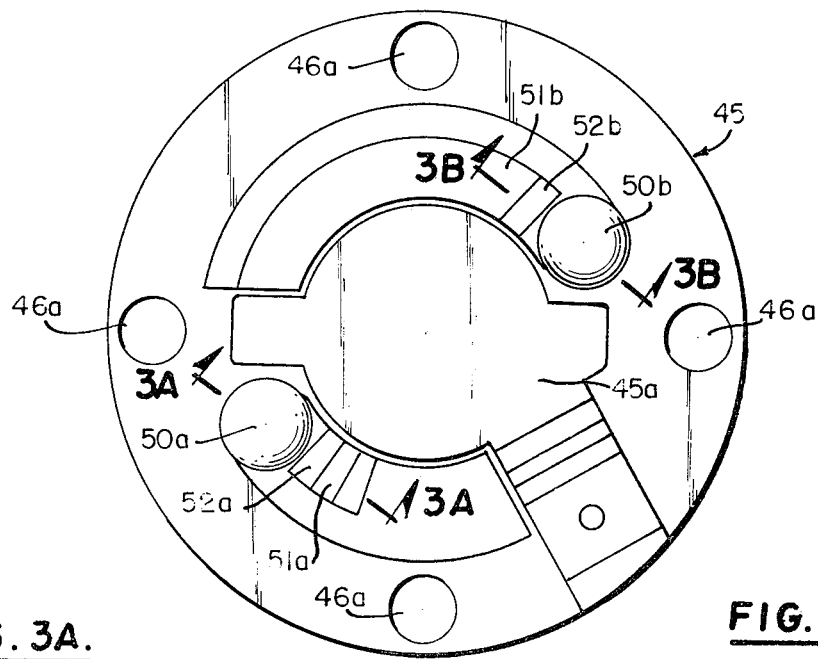
FIG. 2 is an interior view of our novel camplate.
Figure 3A:
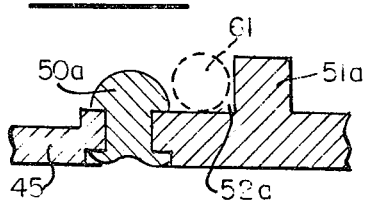
FIGS. 3a and 3b are cross sectional views illustrating the way in which the hemispherical cam surfaces are mounted on the camplate and their proximity to stop members.
Figure 3B:
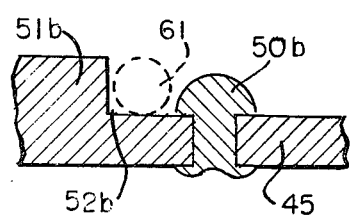
Figure 4:
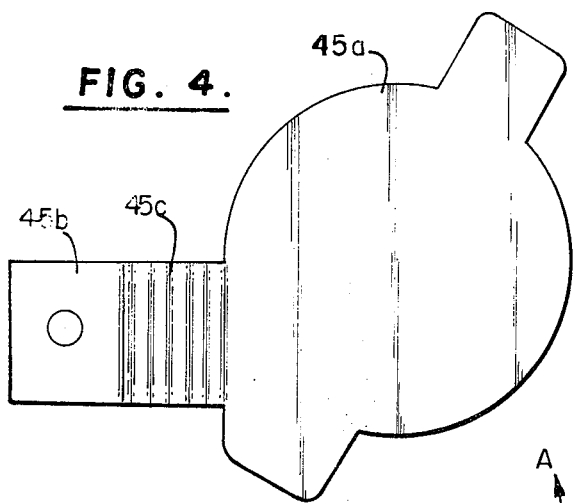
FIG. 4 is a plan view of the door attached to the backside of our cam plate.

One of the improvements that we have made upon the arrangement of U.S. Pat. No. 2,742,052 is illustrated in FIGS. 1 and 2. FIG. 1 is a view of the front side of a camplate member 45 having screw holes 46a, a generally circular keyhole opening 48 and radially extending slots 49a. FIG. 2 is a view of the backside of this same camplate showing the screw holes 46a, hemispherical cam surfaces 50a and 50b (each of which is preferably a rivet, pin or drive-screw of very hard metal, such as a "Driv-lok" rivet, pin or drive-screw composed of hardened stainless steel with a zinc chromate surface finish). The pins 61 of tube 60 will ride up and over these very hard hemispherical surfaces without wearing them down. The pins 61 will then rest in the notch or groove (52a or 52b) that exists between each hemispherical surface (50a, 50b) and an upstanding abutment member or stop (51a and 51b respectively) located closely adjacent thereto, but spaced a short distance therefrom (see FIGS. 2, 3a and 3b).

FIGS. 1, 2, 4 and 5 illustrate another of our improvements over U.S. Pat. No. 2,742,052, namely a one-piece spring biased door member 45a–45b–45c. This door has a first section 45a which is shaped to cover the opening 48a in the cam member, a second section 45b which is designed to be anchored to the cam plate (e.g. by peening) and a third section 45c which interconnects said first and second sections. This third section 45c has a generally corrugated (or undulating) construction so that it acts as a resilient hinge or spring hinge which permits the first section 45a to move backwardly (in the direction of arrow A) from the opening 48a under the entering force of a tube (e.g. such as 60), but which will immediately return to cover the opening 48a because of the biasing action of said third section 45c. Door member 45a is preferably made of beryllium-copper metal that has been age-hardened (e.g. Berylco 25).

Figure 6A:
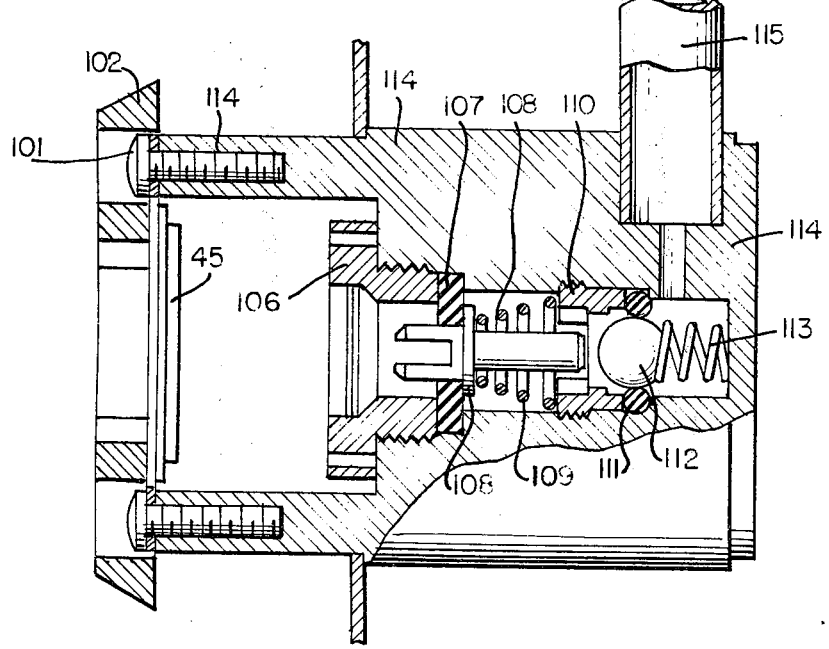
FIG. 6a is a cross sectional view of a camplate service outlet in accordance with our invention and FIG. 6b is an exploded view of this same outlet.
Figure 6B:
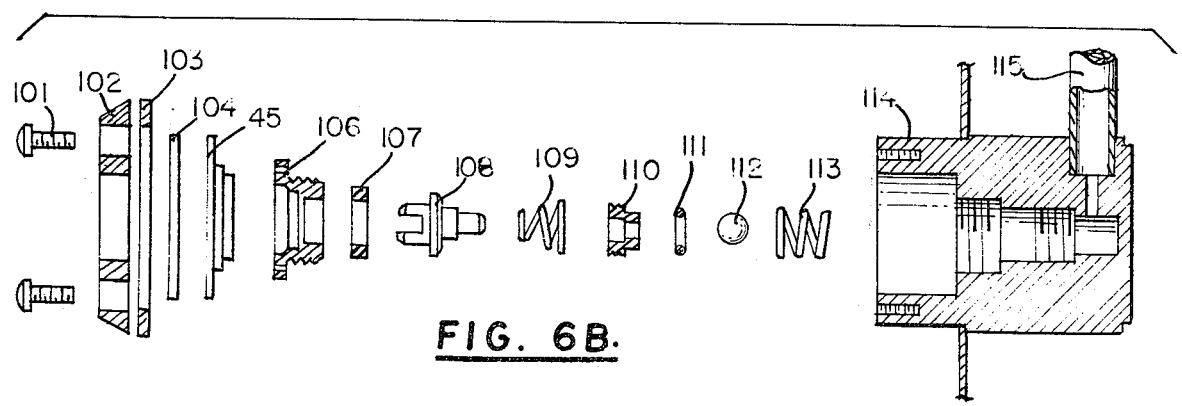

Another very worthwhile feature of our improved valved service outlet is that it does not permit gas to leak back behind the wall structure on which the outlet is mounted. It is very desirable to avoid such leakage because when oxygen does leak at a point behind a wall surface it can accumulate behind the wall into pockets of high concentration, which is a definite fire hazard (particularly in the case of oxygen). Referring now to FIGS. 6a and 6b it will be seen that the main body 114 is composed of a single unthreaded unit which can be easily connected to an oxygen supply pipe 115 by welding. The main body houses inline valves 108 and 112 that are biased to the position shown in FIG. 6a by springs 109 and 113. Valves 108 and 112 are designed to work in sequence and are seated against washer 107 and "O"-ring 111, which are in turn maintained in the desired position by seat retainer bushing 106 and check valve retainer bushing 110. With this arrangement both valves 108 and 112 must leak in order for there to be a leak through the entire unit. The leakage of only one valve would still result in no leakage of gas.

FIGS. 6a and 6b further illustrate the positional relationship of the previously described camplate 45 (see FIGS. 1 and 2) in relation to the remaining components of our improved service outlet. FIG. 6b shows that the camplate 45 is separate from the cover plate 102, which is a distinct improvement over U.S. Pat. No. 2,742,052. With our new arrangement shown in FIG. 6b spacers 103 and 104 may be positioned between the cover plate 102 and the camplate 45 so as to compensate for any irregularities or uneveness that may result in the course of mounting the outlet on a wall.

Figure 7:
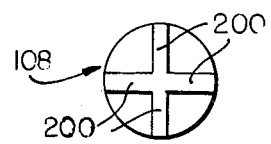
FIG. 7 is an end view of the valve shown in FIG. 6.
Figure 5:
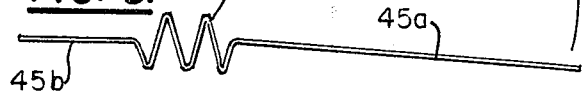
FIG. 5 is a side view of the door shown in FIG. 4.

FIG. 7 is an end view of valve 108, and it will be seen that the crossed slots 200 located in the inlet end of this valve will facilitate ample flow of gas past this valve once the valve has been moved to the right against the pressure of spring 109.

What we claim is:

1. In the known type of valved service outlet for oxygen administration and the like comprising:
   a. a valve body having a longitudinal passage open at one end, closed at the other and having a transverse supply port extending outwardly from the closed end of said passage, b. longitudinally displaceable valve means located intermediate the ends of said longitudinal passageway, which valve means in one position is adapted to permit gas flow through said longitudinal passageway and in the other position block gas flow through said passageway, c. a cover plate secured to the valve body and overlying the open end of the passageway and having an opening for insertion of a connecting tube which is adapted to engage said valve means and to move it longitudinally from one position to another, d. guiding and locking means interiorly of the cover plate for guiding and locking a connecting tube into an inserted position, and e. a door interiorly of the cover plate and overlying the opening therein and swingable inwardly therefrom upon insertion of said connecting tube, the improvement which comprises:

said guiding and locking means comprising at least one hemispherical cam surface composed of very hard metal.

2. A valved service outlet according to claim 1, wherein said hemispherical cam is the head of a rivet.

3. In the known type of valved service outlet for oxygen administration and the like comprising:

a. a valve body having a longitudinal passage open at one end, closed at the other and having a transverse supply port extending outwardly from the closed end of said passage, b. longitudinally displaceable valve means located intermediate the ends of said longitudinal passageway, which valve means in one position is adapted to permit gas flow through said longitudinal passageway and in the other position block gas flow through said passageway, c. a cover plate secured to the valve body and overlying the open end of the passageway and having an opening for insertion of a connecting tube which is adapted to engage said valve means and to move it longitudinally from one position to another, d. guiding and locking means interiorly of the cover plate for guiding and locking a connecting tube into an inserted position, and e. a door interiorly of the cover plate and overlying the opening therein and swingable inwardly therefrom upon insertion of said connecting tube, the improvement which comprises:

said door is composed of a single piece of metal having a first section shaped to cover the open end of said passageway, a second section which is designed to be anchored to a supporting plate, and a third section interconnecting said first and second sections, said third section having a generally corrugated construction so that it acts as a resilient hinge which permits the first section to move backwardly under the entering force of a connecting tube but which will immediately return upon withdrawal of the connecting tube.

4. In the known type of valved service outlet for oxygen administration and the like comprising:

a. a valve body having a longitudinal passage open at one end, closed at the other and having a transverse supply port extending outwardly from the closed end of said passage, b. longitudinally displaceable valve means located intermediate the ends of said longitudinal passageway, which valve means in one position is adapted to permit gas flow through said longitudinal passageway and in the other position block gas flow through said passageway, c. a cover plate secured to the valve body and overlying the open end of the passageway and having an opening for insertion of a connecting tube which is adapted to engage said valve means and to move it longitudinally from one position to another, d. guiding and locking means interiorly of the cover plate for guiding and locking a connecting tube into an inserted position, and e. a door interiorly of the cover plate and overlying the opening therein and swingable inwardly therefrom upon insertion of said connecting tube, the improvement which comprises:

said valve means comprises a linear sequence of two spring loaded valve units that are each designed to press against sealing washers, whereby if one valve unit or washer becomes defective and permits leakage the remaining valve unit will remain operative to prevent undesired leakage.

5. In the known type of valved service outlet for oxygen administration and the like comprising:

a. a valve body having a longitudinal passage open at one end, closed at the other and having a transverse supply port extending outwardly from the closed end of said passage, b. longitudinally displaceable valve means located intermediate the ends of said longitudinal passageway, which valve means in one position is adapted to permit gas flow through said longitudinal passageway and in the other position block gas flow through said passageway, c. a cover plate secured to the valve body and overlying the open end of the passageway and having an opening for insertion of a connecting tube which is adapted to engage said valve means and to move it longitudinally from one position to another, d. guiding and locking means interiorly of the cover plate for guiding and locking a connecting tube into an inserted position, and e. a door interiorly of the cover plate and overlying the opening therein and swingable inwardly therefrom upon insertion of said connecting tube, the improvement which comprises:

said valve body is of unitary construction so as to prevent leakage of gas at any point intermediate its ends.

* * * * *